(12) United States Patent
Bianconi et al.

(10) Patent No.: US 9,724,054 B2
(45) Date of Patent: Aug. 8, 2017

(54) CRANIOSTAT FOR ACQUIRING EXTRAORAL DENTAL RADIOGRAPHIES

(71) Applicants: Davide Bianconi, Cesena (IT); Andrea Geminiani, Imola (IT); Gianluca Manuzzato, Imola (IT)

(72) Inventors: Davide Bianconi, Cesena (IT); Andrea Geminiani, Imola (IT); Gianluca Manuzzato, Imola (IT)

(73) Assignee: CEFLA SOCIETÁ COOPERATIVA, Imola (BO) (IT)

( * ) Notice: Subject to any disclaimer, the term of this patent is extended or adjusted under 35 U.S.C. 154(b) by 62 days.

(21) Appl. No.: 14/685,715

(22) Filed: Apr. 14, 2015

(65) Prior Publication Data
US 2015/0297153 A1    Oct. 22, 2015

(30) Foreign Application Priority Data

Apr. 17, 2014    (IT) .............................. BO2014A0219

(51) Int. Cl.
*A61B 6/14*    (2006.01)
*A61B 6/04*    (2006.01)
*A61B 6/00*    (2006.01)

(52) U.S. Cl.
CPC .................. *A61B 6/14* (2013.01); *A61B 6/04* (2013.01); *A61B 6/501* (2013.01)

(58) Field of Classification Search
CPC ................................... A61B 6/04; A61B 6/14
See application file for complete search history.

(56) References Cited

U.S. PATENT DOCUMENTS

| | | | | |
|---|---|---|---|---|
| 2004/0045551 A1* | 3/2004 | Eaton | .................... | A61M 16/06 128/206.21 |
| 2009/0175409 A1* | 7/2009 | Stockl | ...................... | A61B 6/04 378/38 |
| 2012/0321051 A1* | 12/2012 | Jarva | ........................ | A61B 6/14 378/208 |
| 2014/0147803 A1* | 5/2014 | Lecuyer | ................. | A61B 6/107 433/29 |

FOREIGN PATENT DOCUMENTS

| | | |
|---|---|---|
| JP | 2004275512 A | 10/2004 |
| JP | 2013244146 A | 12/2013 |
| WO | WO2013014488 A1 | 1/2013 |

* cited by examiner

*Primary Examiner* — Wyatt Stoffa
*Assistant Examiner* — Eliza Osenbaugh-Stewar
(74) *Attorney, Agent, or Firm* — Themis Law (57) ABSTRACT

A craniostat for an extraoral dental radiographic apparatus includes an upper portion connected to a lower portion by two rods. The upper portion includes a rest for a patient's forehead, wherein the rest for the patient's forehead rest has an arched shape vertically sliding in a suitable seat inside a crossbeam supported by the rods. A method of use of a craniostat according to the invention is also described.

11 Claims, 11 Drawing Sheets

CRANIOSTAT FOR ACQUIRING EXTRAORAL DENTAL RADIOGRAPHIES

FIELD OF THE INVENTION

The present invention relates to extraoral dental digital radiographic apparatuses, wherein both the X-ray source and the X-ray sensor are placed outside a patient's oral cavity. In particular, the present invention relates to a device for immobilizing a patient's head during radiographic acquisitions. Said positioning device is known in the art under the name of craniostat.

BACKGROUND OF THE INVENTION

Extraoral dental radiographic apparatuses can produce two kinds of radiographies: bi-dimensional (2D) radiographies, or volumetric (3D) radiographies.

In the field of bi-dimensional radiographies, panoramic radiographies and teleradiographies are included.

Panoramic radiography (also known as orthopantomography) produces a radiographic image of a curved plan, known as Welander's curve, approximating a patient's jaws, with blurring of the anatomical structures laying outside a narrow layer around the predesigned curved plane. This technology has been known since the '50s.

Teleradiography is a projective radiographic technique, producing radiographic images of the skull or of other anatomical areas from different projections, with minimum magnification and geometrical distortion. Usually two perspectives are represented, latero-lateral and anterioposterior.

Cone beam volumetric radiography (also known as CBCT) is the acquisition, from different projection angles, of a series of bi-dimensional radiographic images which will be processed post-acquisition to reconstruct three-dimensional volumes.

Extraoral radiographies are performed through known apparatuses, wherein typically at the two ends of a C-arm an X-ray source and an X-ray sensor are positioned, respectively, while a patient is placed between them. Typically the X-ray source and sensor rotate around patient's head, which is kept still by a positioning device (craniostat). The movements that mechanical parts have to perform in order to get this result is called trajectory.

In order to get a good image, the patient must remain still during the acquisition time, that is during X-ray emission. On the other hand, it is easy to realize that the patient will stand still if she/he is comfortable, while if she/he is uncomfortable, or under stress, there are more probabilities for her/him to move.

Another important point is that the craniostat should be as transparent as possible to X-rays, in order not to create artifacts which might reduce the diagnostic validity of the radiographic image. This has an impact on materials (no metallic materials can be used), but also on thicknesses, in that with increasing thickness even a radiolucent material begins to appear in radiographies. However, the reduction of thickness bears the risk of making the craniostat not rigid enough to ensure the solidity of the object and therefore the patient's immobility.

Moreover, as there is physical contact between patient and immobilizing device, the contact parts of the craniostat must be disposable, or must be disinfectable between patients.

For safety reasons it is important that electric parts (cables, motors, actuators, sensors) are not in the close proximity of the patient.

The craniostat must allow the positioning of any patient: from pediatric patients to adult patients of big dimensions (99 percentile), and therefore must fit cranial measures presenting a wide variability (cranium diameter going from 14 cm to 18.5 cm).

In order to perform all the kinds of acquisitions which will be described in the following, the extraoral dental radiographic apparatus must be able to perform an ample number of different trajectories, and therefore the C-arm needs wide possibilities of movement around the patient. Trajectories have a generically circular or semi-circular shape, and it is therefore possible to define an "anti-collision cylinder" wherein neither X-ray source nor X-ray sensor can enter. Once defined an as small as possible anti-collision cylinder, both the patient's head and craniostat must be contained inside it. It is therefore important that the craniostat is not bulky, so as to not constitute a limit for the trajectories.

In order to perform all the kinds of acquisition, especially teleradiographies, the craniostat has to be removed by X-ray path during the acquisition.

Finally, the craniostat must allow a rapid and easy positioning of the patient by the professional human operator.

To define the correct positioning of the patient's head, referring to anatomical portions and also to virtual planes which are defined on the basis of anatomical portions is necessary. The main and most widely known is Frankfurt plane, which is a virtual plane passing through the inferior margin of the left orbit and the upper margin of each ear canal or external auditory meatus, immediately under the eye.

In the family of panoramic radiographies there are different kinds of acquisitions, which are all obtained through blurring of anatomic structures outside a limited layer around a predefined plane. Each of this kind of acquisition has specific requirements for positioning the patient. To recapitulate only the main kinds of acquisitions:

Panoramic radiographies or orthopantomographies: the patient is usually oriented with her/his Frankfurt plane placed horizontally and in a sagittally symmetric position with respect to the acquisition trajectory. The two dental arches must not be overlapping as in the normal occlusal position, but to avoid overlapping in the image, they must be vertically pulled away on the same plane, in order to be sure that they are in the focal trough.

Latero-lateral Temporomandibular Joints (TMJ): in this case the focal plane sagittally cuts the condyle head. The preferred positioning is always with the Frankfurt plane placed horizontally. In order to have an effective diagnosis, often it is necessary to repeat consecutively the same acquisition, one with open mouth, one while the patient is occluding, without repositioning the patient.

Frontal or postero-anterior Temporomandibular Joints (TMJ): in this case the focal plane coronally cuts the condyle head. The preferred positioning is with the plane passing from the upper margin of the ear canal to the superciliary arch positioned horizontally (the head is inclined forward). In order to have an effective diagnosis, often it is necessary to repeat consecutively the same acquisition, one with open mouth, one while the patient is occluding, without repositioning the patient.

Bite-wing: this is a projection very similar to panoramic projection, but instead of acquiring dental arches in their complete height, the image is limited to the coronal portion of teeth. The patient must be placed as in the panoramic acquisition, but it being a very restricted field, the bite must be at a pre-defined height.

In three-dimensional acquisitions all the field of view is reconstructed, so it is important that the anatomic portion is analyzed is in the centre of the field of view. Especially for small fields of view (around 5 cm high), it might be important to align the patient with the mandibular plane placed horizontally, the mandibular plane ideally passing from chin end to mandible angle. In this way possible metallic artefacts remain on the plane of dental crowns, and especially third molars are on the same plane of incisors.

In a typical extraoral apparatus, the number of different acquisition programs is around thirty; all these programs are variations of the main kind of programs recapitulated above. A well-made craniostat should allow the acquisition of all the kinds of images necessary for diagnostic aims.

SUMMARY OF THE INVENTION

An aim of the present invention is to provide a craniostat according to the above-mentioned requirements, which is of easy and economic manufacture.

This object is achieved by an apparatus and a method having the features of the independent claims. Advantageous embodiment and refinements are specified in the claims dependent thereon.

A craniostat according to the present invention is an integral object removably mounted on a specific support. The craniostat can be removed from said support, the removal being necessary during apparatus calibration and when teleradiographies are performed, as the craniostat is on the X-ray path (during teleradiographies the patient is blocked by another specific positioning device). The removing system must be simple and ergonomic for the operator, without undermining the necessary stability of the craniostat while it is in use. In a craniostat according to the present invention, the coupling craniostat-support is produced with four pins, which enter into four specific pin holes, one of which is longer than the others.

For the sake of clarity, the craniostat can be subdivided into two portions:

Lower portion for supporting the patient's chin and bite;
Upper portion for blocking the patient's forehead and temples.

The perfect immobilization of the patient is obtained through the cooperation of both portions.

The lower portion of the craniostat comprises a supporting base for fixed or removable parts supporting different anatomic portions of the patient: rods supporting the upper portion of the craniostat, bite for the patient, chin support and other supports for different kinds of acquisitions. The lower base exhibits a recess towards the patient which is useful to acquire temporomandibular radiographies with both open and closed mouth.

The lower base brings a bite having a height adjustable with respect to the base itself, correspondently to the needs of the specific acquisition needs and of the patient's anatomy. The bite is height adjustable, and must be blocked at different heights. The bite can be continuously blocked at any height comprised between a minimum and a maximum (no pre-defined heights are present); for the bite-wing position only a pre-defined height is required. A small lever loaded by a spring indicates to the operator that the correct height was reached, without the need of indications on bite stem, like notches or colored points of reference, which must be optically checked by the operator.

The shape of the bite must be such to ensure the smallest radiopacity; for this an arch shape was chosen, instead of a L-shape. Typically the bite is used with a disposable cover for the patient's hygiene, which is changed between patients; the bite is made of only one material, and is optionally autoclavable.

The thickness of the material is as low as possible to ensure radiolucency, so as not to visualize the bite in the radiographic image.

The adjustment of bite height is free; once the desired height was reached, the bite is blocked in the correct position through a lever positioned in the anterior part of the base.

The bite, until it is blocked, freely rotates in its seat, and this facilitates the patient's positioning; however, when the bite is blocked in its correct height through its lever, is also automatically centered, so as to ensure that the patient is correctly positioned on the sagittal plane.

According to an embodiment, the bite is blocked in the desired position through a lever, which, in addition to blocking the bite in the vertical direction, sagittally rotates the bite itself bringing it in a position symmetrical to the sagittal plane.

From the base two rods branch, supporting the upper portion of the craniostat; the distance between the bite point and the rods is the shortest possible to allow the passage of the sensor without collision, but at the same time ensuring that rods are outside the acquisition plane, therefore in the blurred area.

The chin support is also removable, to allow the maximal versatility of use of the craniostat (open mouth acquisition of temporomandibular joints). The coupling occurs through two pins, having the same length.

Concerning the upper part of the craniostat, its adjusting mechanisms work through friction, which allows them to be spring free. This is advantageous in that the craniostat can be made of plastic materials, so ensuring radiolucency and preventing scattering artefacts due to metal.

The plurality of supporting points for the patient's head makes the positioning comfortable for the patient, and nonetheless very stable.

The difference in diameter between a very large patient and the anti-collision cylinder is very limited, about 2-3 cm. Therefore, the limited thickness of the craniostat allows both to perform complex trajectories, and to obtain the maximal radiolucency of the craniostat in radiographies.

In a craniostat according to the present invention, a positioning philosophy may be chosen that is different from the system making use of an electromagnet or pre-loaded springs. In such systems, the craniostat holding capability is in the first case dependent on how much the operator tightens the adjusting mechanisms, in the second case on how much the spring is pre-loaded. Therefore, such objects are very stable but also very rigid, and not very comfortable for the patient. On the other hand, in a craniostat according to, the present invention the adjusting systems may operate so that first the operator approaches the contact points to the patient, and then blocks the contact point in that position, allowing an adjustment that is much more respectful of the patient's anatomy and comfort. The operator gets a tactile and/or acoustic feed-back for each adjustment.

BRIEF DESCRIPTION OF THE DRAWINGS

Further advantages and properties of the present invention are disclosed in the following description, in which exemplary embodiments of the present invention are explained in detail based on the enclosed drawings:

(FIG. 7a), top view (FIG. 7b) and perspective view (FIG. 7c);

DETAILED DESCRIPTION OF EMBODIMENTS OF THE INVENTION

Figure 1:
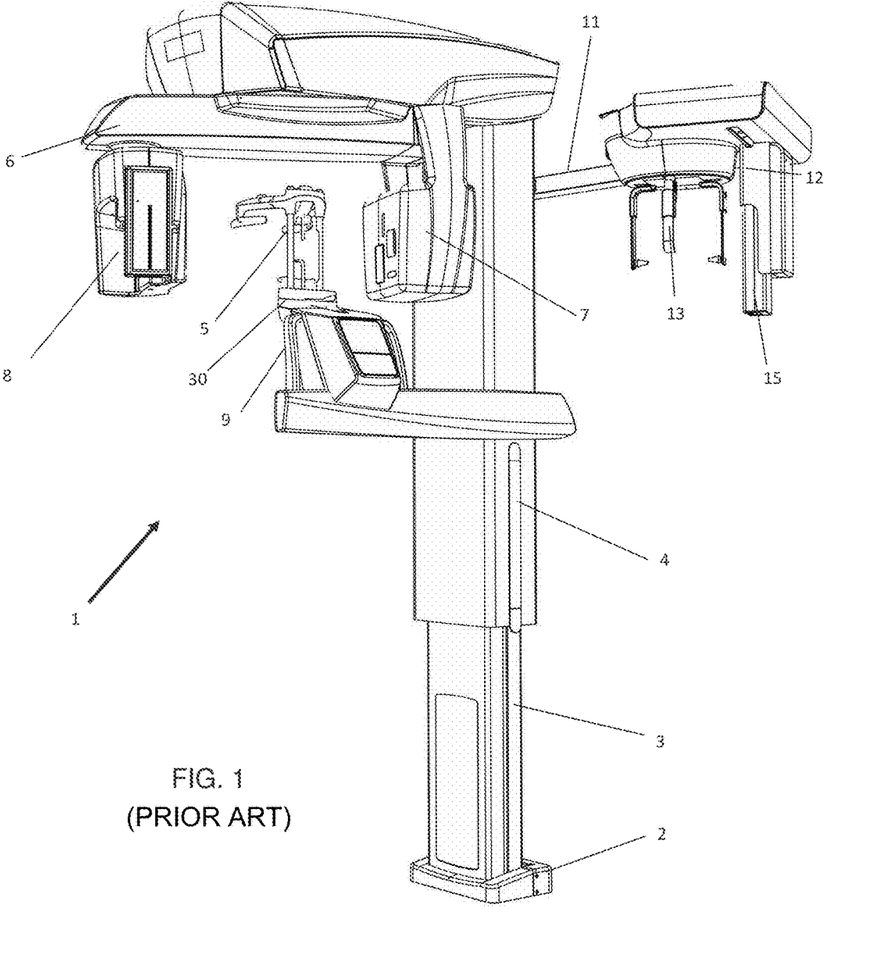
FIG. 1: Perspective view of an apparatus for acquiring panoramic, volumetric, and teleradiographic images in the prior art.

FIG. 1 shows a typical extraoral radiographic apparatus 1 in the known art, comprising an X-ray source 7 projecting a collimated bundle of X-rays through a patient (not shown); a bi-dimensional X-ray sensor 8 positioned to measure the intensity of X-rays after they crossed the patient; a device 5 for the positioning of the patient interposed between X-ray source and sensor; a C-arm 6 on whose ends said X-ray source 7 and sensor 8 are supported; a mechanical system allowing the rotation and the translation of said C-arm around the patient, in order to acquire radiographic images from various positions; electronic circuits (not shown) that adjust and synchronize the workings of the various parts of the apparatus. The position of the C-arm 6 can be adjusted to a patient's height thanks to column 4 sliding on columns 3 fixed to the ground through base 2. The extraoral apparatus 1 may further comprise an arm 11 for teleradiography, to which another patient's positioning device 13 is fixed, and a teleradiography sensor 15 is removably fixed on support 12.

Figure 2:
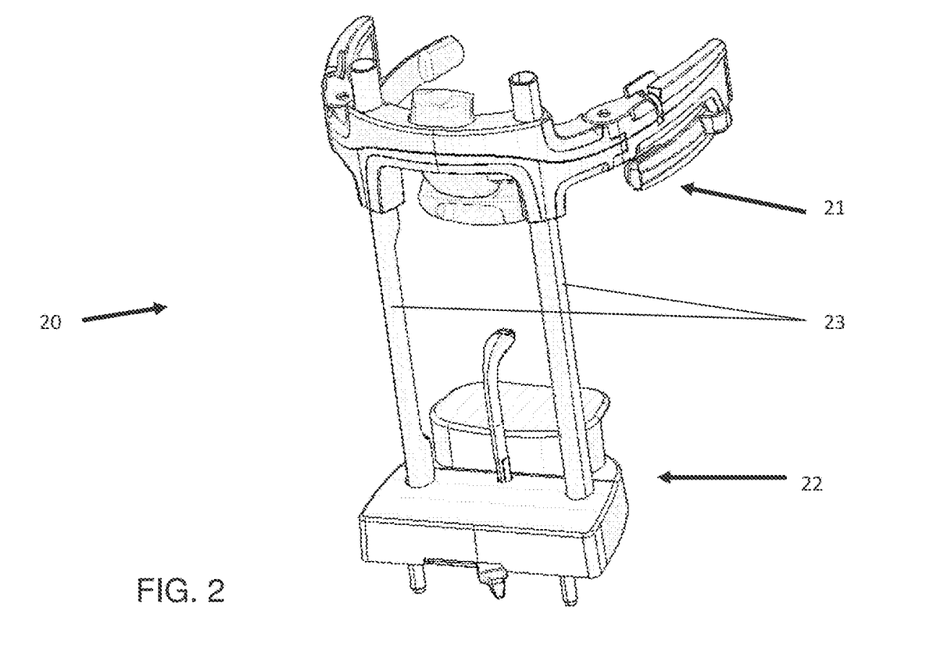
FIG. 2: Perspective view of a craniostat according to the present invention.
Figure 3:
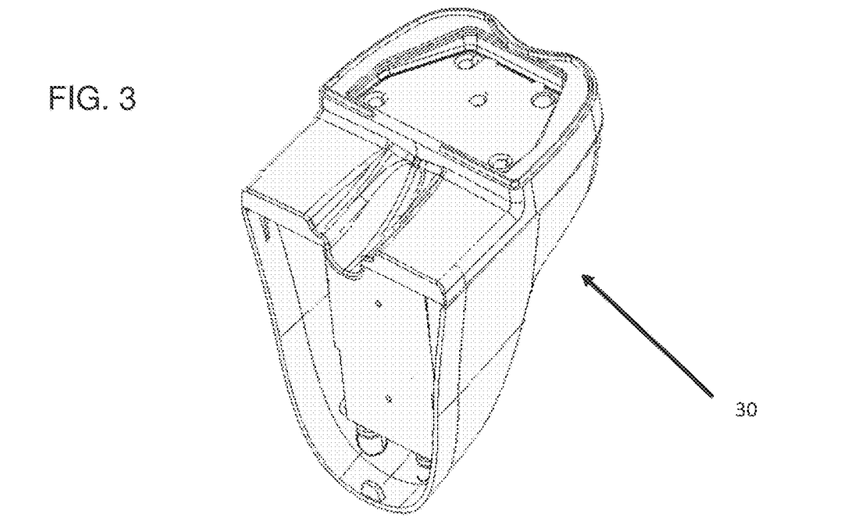
FIG. 3: Perspective view of a support of the craniostat.

A craniostat 20 according to the present invention is shown in FIG. 2 disconnected from the apparatus 1 for acquiring radiographs; when it is connected, it is in the position indicated with 5 in FIG. 1. The craniostat is placed on its specific support 30, which is part of the patient positioning device 5; the support 30 is shown in FIG. 3.

Figure 4:
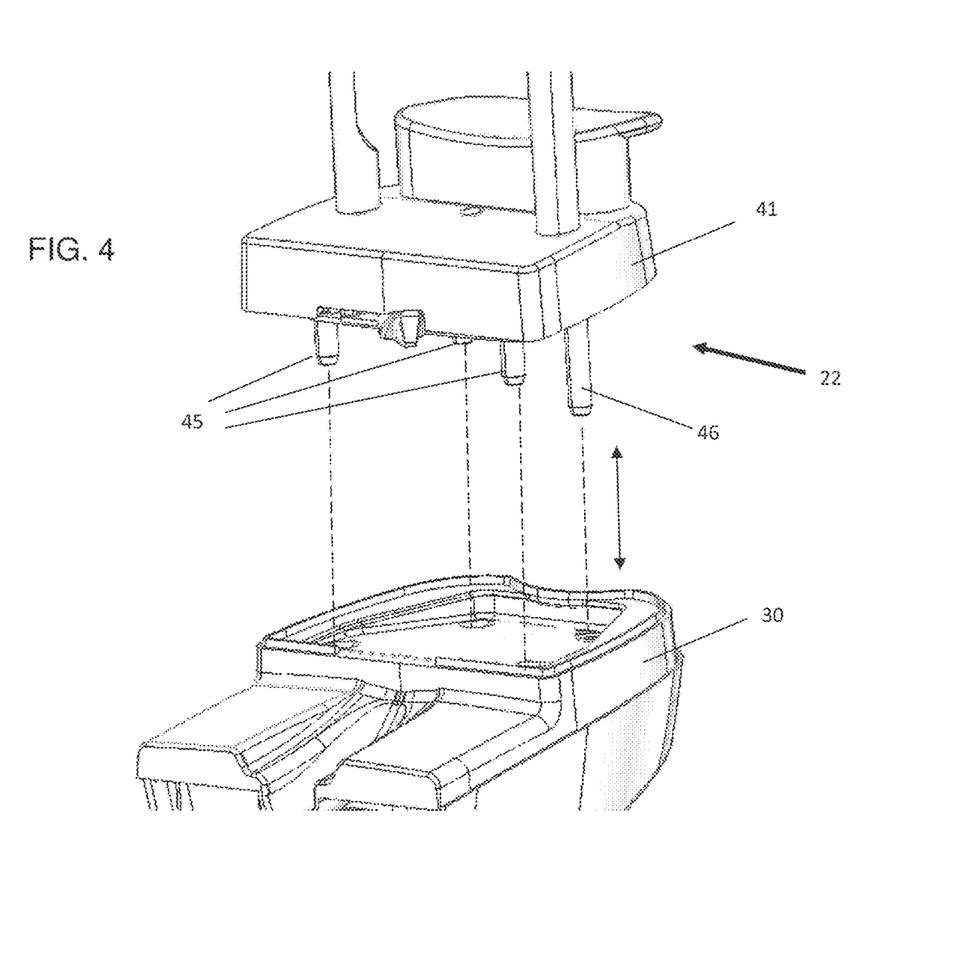
FIG. 4: Detail of the coupling between the craniostat lower portion and its support connecting it to the apparatus.

FIG. 4 shows the coupling between the lower portion 22 of the craniostat 20 and the support 30 connecting it to the apparatus 1. The coupling craniostat-support is realized through four pins 45, 46 which fit in their specific holes; one of the pins is longer than the others. The longer pin 46 is the one ensuring the best coupling precision, thanks to minimal coupling tolerance in the respective hole, while the correct positioning and stability of the craniostat are ensured by the remaining shorter pins 45. The choice of different coupling tolerances is linked to production cost and to the ease of coupling by the human operator. A spring-loaded pressure plate acts on the pins, so as to inform the human operator that the perfect coupling craniostat-support has been reached, which ensures maximum stability. The spring is compressed when the pin 46 is inserted in its hole for its complete length, and its operation gives the operator an acoustic (metallic click) and tactile (friction of the vertical movement) feed-back. The spring-loaded pressure plate is indispensable on the long pin 46 and optional on the three short pins 45.

For the sake of clarity, as shown in FIG. 2 the craniostat 20 can be subdivided into an upper portion 21 and a lower portion 22. A couple of rods 23 connects the two portions 21 and 22. In the immediately following paragraphs the lower portion of the craniostat will be described.

Figure 5:
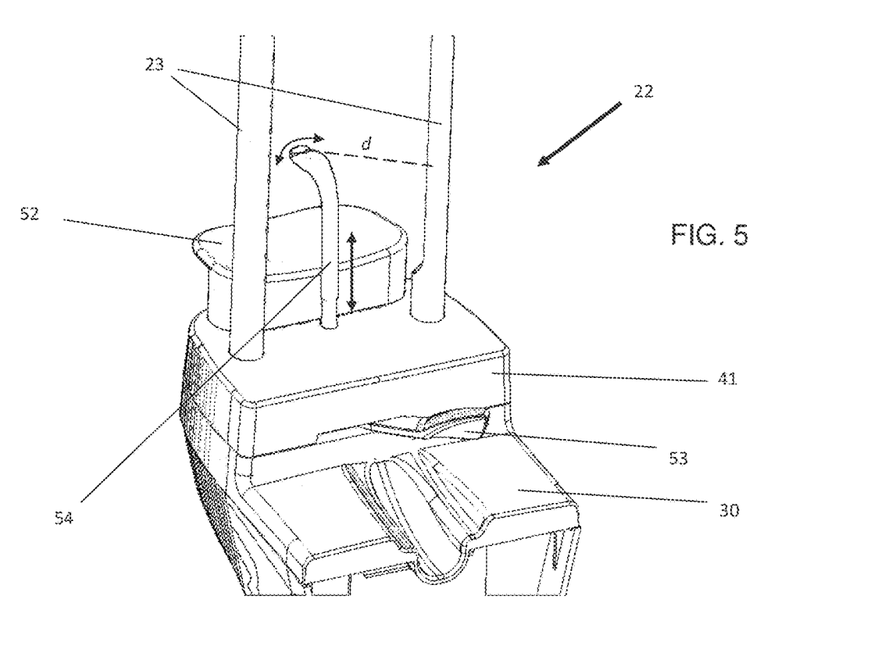
FIG. 5: View of the lower portion of the craniostat.

In FIG. 5, the lower portion of the craniostat 20 is shown resting on support 30 and complete with chin rest 52. The lower portion 22 of the craniostat has a fixed base 41, provided with a lever 53 for blocking bite 54. The chin rest 52, and the bite 54 are removable according to the needs of the different acquisitions.

The distance d between bite 54 in its blocked position and rods 23, indicated with a dotted line, is the widest possible so as rods 23 are out from the focal trough, but inside the anti-collision cylinder. In the preferred embodiment, said distance d is 55 mm.

When the lever 53 is its unblocked position (in one of its two extreme positions, e.g. totally on the left), the bite 54 is free to vertically slide in the direction indicated by the linear double arrow, and to pivot in the direction indicated by the arched double arrow. This disposition is particularly comfortable when positioning a patient, in that the human operator firstly unblocks the bite 54 through the lever 53 and rotates it toward one of the two rods 23, rests the patient's chin on chin rest 52, and then positions the bite 54 inside the patient's oral cavity vertically adjusting it. When the operator blocks the position of the bite 54 through lever 53, e.g. bringing the lever totally on the right, the bite 54 is automatically positioned in its correct sagittal position, thanks to its particular shape.

Figure 6:
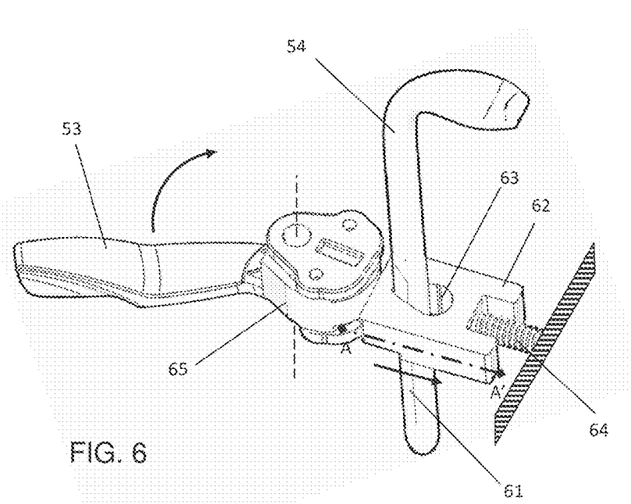
FIGS. 6 and 6a: Details of the block mechanism of bite in an assembled view (FIG. 6) and according to section A-A' (FIG. 6a)

FIG. 6 shows the mechanism, contained in the base 41, for blocking the bite 54. When the lever 53 is in its unblocked position, the stem 61 is in the portion having a circular section of the hole 63 of block 62, and is therefore free to move. When the lever 53 is in its blocked position, the block 62 is pushed by a cam 65 so as to compress spring 64 in the direction of the arrow. The portion of the hole 63 having a triangular section is coupled to the stem 61, blocking it through friction. The stem 61 has in its turn a triangular transversal section, which allows both a higher friction, and an auto-centering on the sagittal plane. The axis A-A' shows the plane of the section shown in FIG. 6a and allows to better appreciate the functioning of the block. The hole 63 has a section partly rounded and partly triangular, and the stem 61 has a triangular section which, when blocked, is coupled to the triangular portion of hole 63. When the lever 53 is brought in the unblocked position again, the cam 65 is rotated and the spring 64 pushes in a direction contrary to the arrow the block 62, freeing the coupling between the triangular section of hole 63 and of stem 61 of bite 54.

Figure 6A:
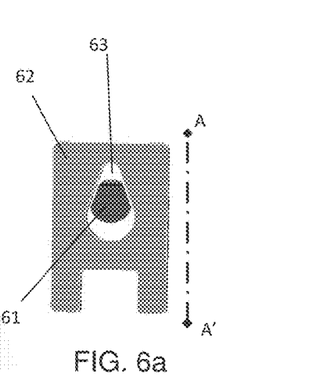

As can be seen from the Figures, triangular section means that a part of the delimitation surfaces of the hole, at least for a certain axial length of the bite itself, have two walls which are opposed and converging. These walls are preferably symmetrically positioned with respect to a plane containing the longitudinal axis and a diameter of hole 63, such diameter coincides with a bisector of the angle defined by the two opposed converging walls.

The remaining part of the perimetric delimitation surface of hole 63 can have any shape, and in this embodiment is cylindrical, i.e. having circular section; the wedge-shaped portion and the cylindrical portion are seamlessly joined together.

The stem 61 has at least for a part of its axial, longitudinal extension a section substantially analogous to the section of hole 63, but dimensionally smaller and such that said stem 61 can slide both axially, in order to adjust the bite height with respect to the chin rest, and radially, i.e. in the direction of wedging a portion of the surface of the stem itself. The stem has two opposed and converging walls like a wedge, preferably with the same angle of the converging walls of hole 63, also in the opposed direction of said walls, moving from the converging walls of hole 63.

The tightening means, i.e. the mechanism controlled by the lever, thrust the stem in the wedging direction of the wedge-shaped portion of said stem into the wedge-shaped portion of the hole 63, blocking said stem both in the axial direction and in its rotation around its own longitudinal axis. At the same time, while in the not tightened condition of the stem 61 in the hole 63 the stem 61 is free both to axially slide and also to rotate around its own axis, in the above-described tightened condition, not only the stem is blocked as regards its rotation, but thanks to the substantially wedge-shaped shape of the stem 61 and of hole 63, said stem and therefore the wedge-shaped section of the bite are forced in the desired centering position, defined by the shapes and orientation of the wedge-shaped surfaces of both hole 63 an stem 61.

The general concept expressed by the described forms of the present embodiment consists therefore in the fact that both the stem 61 and its housing hole 63 have both complementary surfaces of contact having a pre-defined angular orientation and a shape so as in tightening conditions of stem 61 in the hole 63: said surfaces come into contact and define a pre-defined angular orientation of the stem around its own axis.

Figure 7:
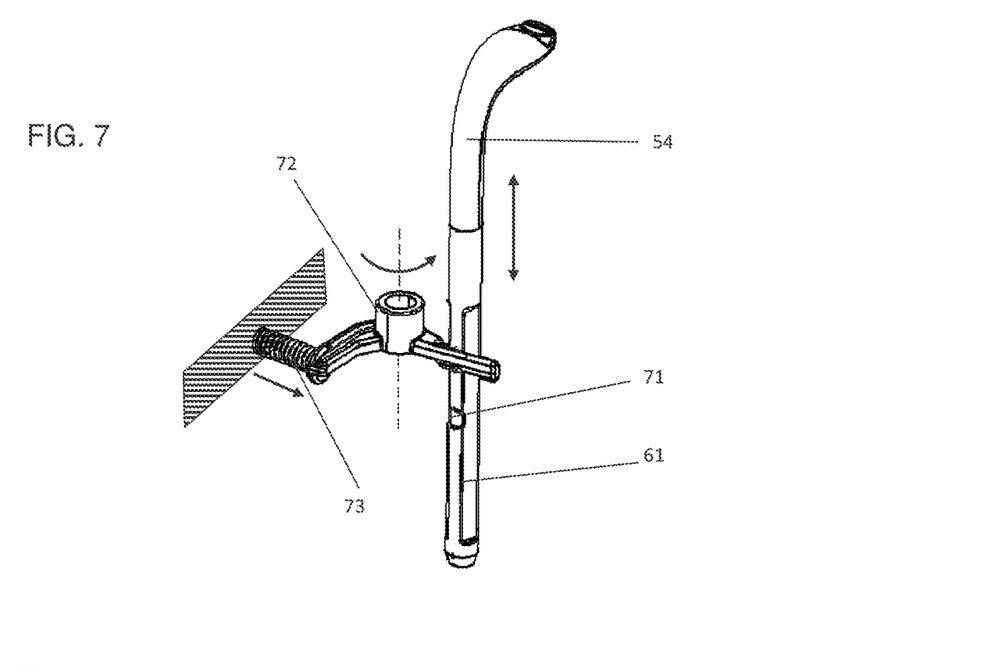
FIGS. 7, 7a, 7b, Details of the bite stem in assembled view (FIG. 7), side view and 7c.

FIG. 7 shows a further detail of bite 54, which is particularly useful when acquiring bite-wing radiographies, which requires the positioning of the patient at a pre-defined height. To this aim, the stem 61 of bite 54 has a particular profile of its transversal section. The upper part has a substantially circular section, while about halfway its lower section becomes triangular or wedge-shaped, for the reasons explained above linked to bite auto-centering. Moreover, at a pre-defined height, the stem 61 has a horizontal recess 71. Inside base 41 there is also a small lever 72 pre-loaded by a spring 73, which constantly frictions, in a virtually undetectable way, against the stem 61. When the recess 71 is brought in correspondence of the small lever 72, there is an acoustic and tactile feed-back for the operator, who is informed of the precise reaching of the position for bite-wing acquisitions. The block of the bite 54, also for bite-wing positions, occurs through the lever 53.

Figure 7A:
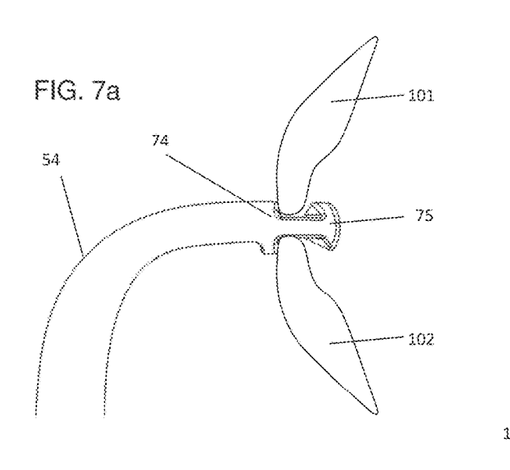
Figure 7B:
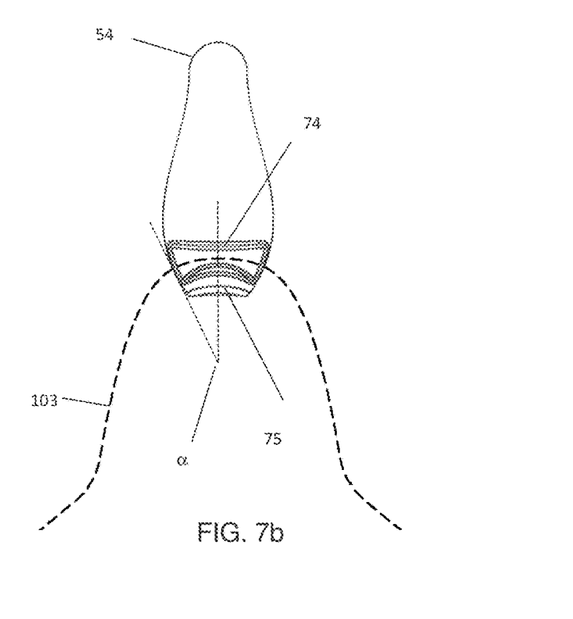

FIG. 7a shows the sagittal section of bite 54 which is kept between the patient's teeth, while FIG. 7b shows a top view of the bite 54 end. The portion that the patient bites with her/his incisors is small. In the FIG. 7a the anterior part 74 of the portion is shown, which has a net, not blunted angle, so as to ensure the stop of upper 101 and lower incisors 102, which thus lie on the same plane; in this way a panoramic image results with an as correct as possible focusing. On the other hand, the posterior part 75 is tapered and rounded to better fit the patient's anatomy (Welander curve 103) and to reduce the thickness of the material crossed by X-rays. This tapering, indicated with angle α in FIG. 7b, must nonetheless ensure a resting position sufficient for anterior teeth. In the preferred embodiment said angle α is comprised between 15 and 25 degrees.

Figure 7C:
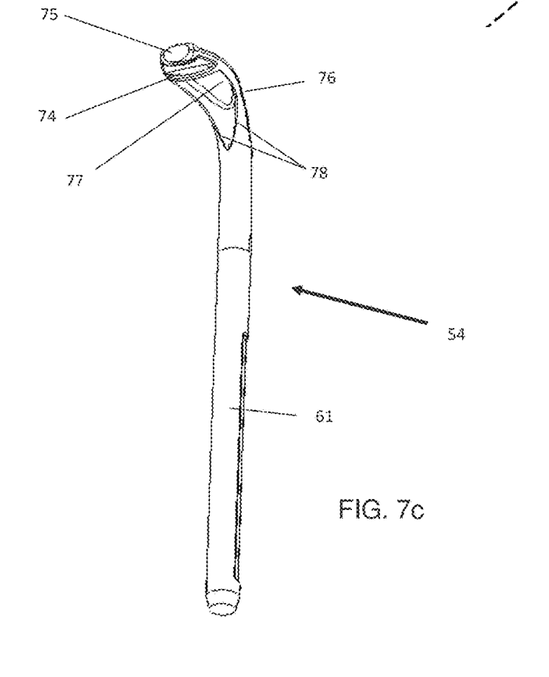

Concerning the bite 54, it was optimized to the aim of not appearing in the radiographies, yielding an artifact. Therefore, it was built using a radiolucent plastic material. Moreover, its profile has a particular shape which allows to minimize the quantity of plastic material. As can be seen in FIG. 7c, in the lower side of the arched part 76 of the bite there is a recess 77 which reduces the thickness of the bite. With the aim of maintaining its rigidity, in the bite 54 there are two ribs 78 distinct in the bite distal part, which unite in the proximal part; on said ribs the stress transmitted by the patient is discharged.

Figure 8:
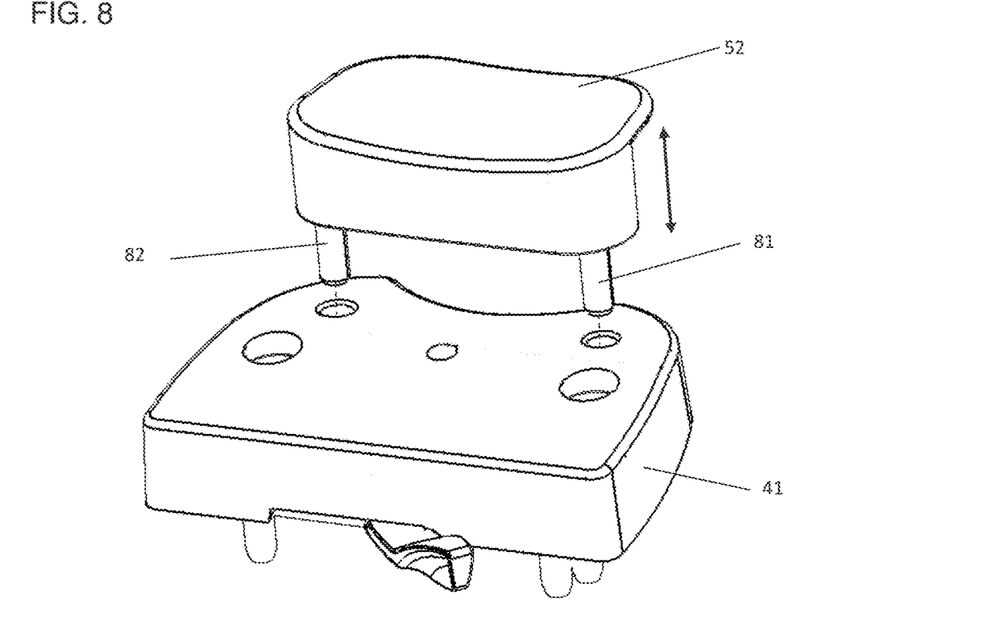
FIG. 8: Details of the coupling system between chin support and craniostat base.

In FIG. 8 the coupling between chin rest 52 and base 41 is shown. The coupling occurs through two pins 81 and 82 having the same length; the pin 81 is inserted in a hole which has a reduced coupling tolerance. The fact that the coupling of pin 82 is looser allows the operator to easily insert it into its hole, while the precise coupling of pin 81 ensures the stability of the assembly. The weight of the patient's head is sufficient to ensure the desired immobility, and therefore there is no spring-loaded pressure plate or similar devices. The presence of chin rest 52 is required in practically all acquisitions, but those of temporomandibular joints, during which chin rest 52 must be removed.

Figure 9:
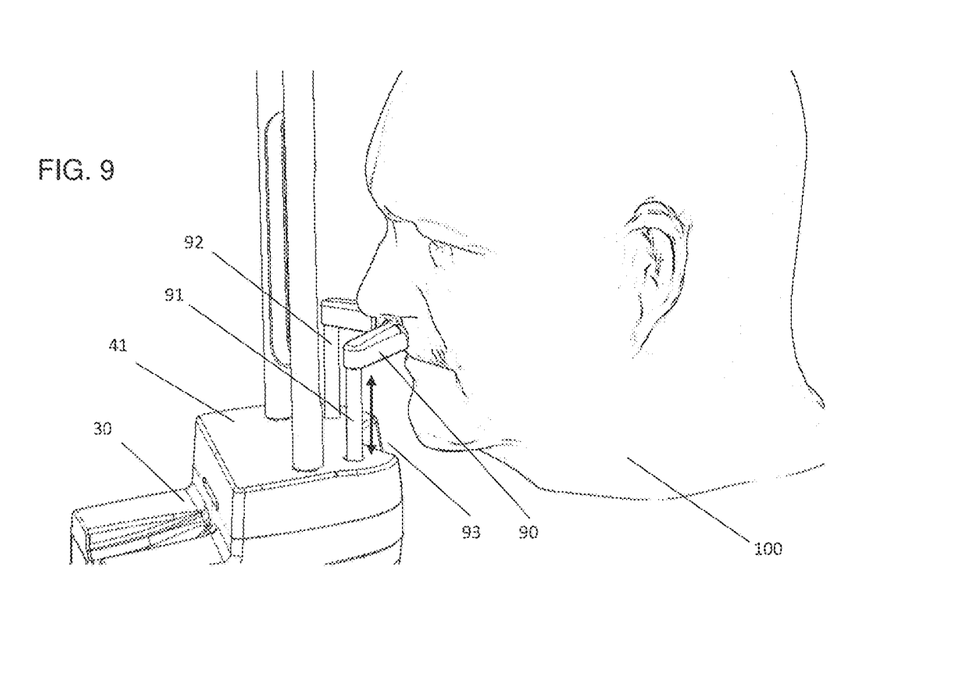
FIG. 9: Detail of the nasal support.

In general terms, when chin rest 52 is removed, it is replaced by nose support 90, on which the patient rests her/his anterior nasal spine as shown in FIG. 9. The nose support 90 is inserted through two pins 91 and 92 in the same holes in which pins 81 and 82 of chin rest 52 are inserted, with the same tolerances discussed above. When patient 100 rests on nose support 90, a recess 93, on the craniostat 20 base 41, allows her/him to easily open and close her/his mouth, without the need of re-positioning the patient.

In the immediately following paragraphs the upper portion of the craniostat will be described in detail. The upper portion of the craniostat has to keep the patient in the desired position, and the most suitable points to this aim are considered the patient's forehead (on the sagittal plane), the lateral parts of the cranium (laterally), the terminal part of the parietal bone (posteriorly).

Figure 10:
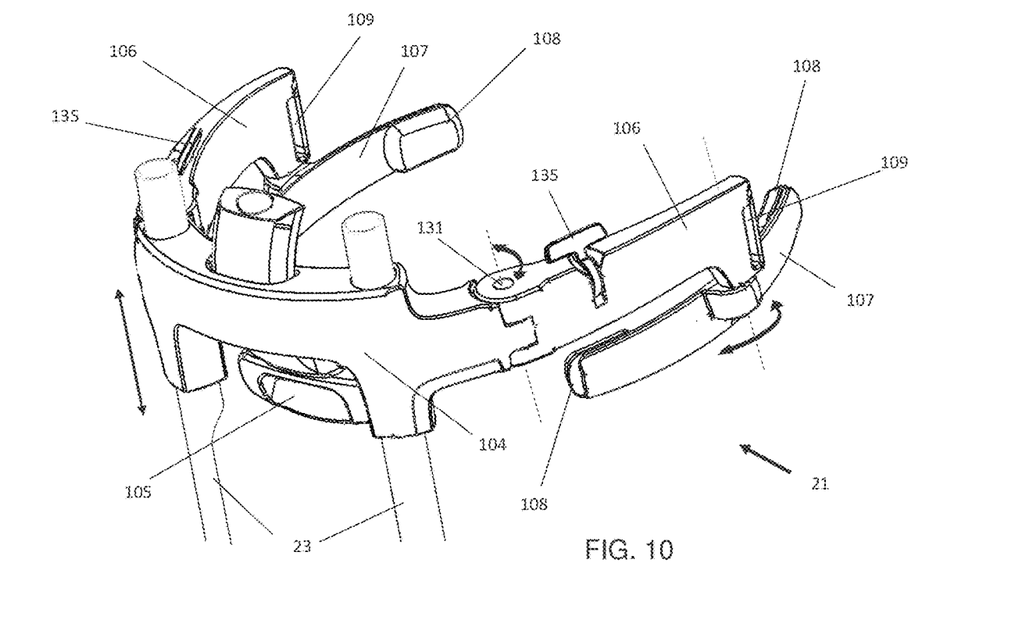
FIG. 10: Perspective view of the upper part of the craniostat.

In FIG. 10 the upper portion 21 of the craniostat is shown, comprising a forehead rest 105 and two mobile rests 107 for the lateral portions of cranium. The upper portion 21 is height adjustable on rods 23. In particular, the upper portion 21 comprises a crossbeam 104, having holes which allow to slide on rods 23. On crossbeam 104 there is a hole in which the forehead rest 105 is slidingly inserted.

Also on the crossbeam 104 there are connected two small arms 106, which can pivot independently of one another, so as to adjust to the width of the patient's cranium, accommodating also patients having remarkable dissymmetry. At the end of the two arms 106 there are two small arches 107, free to independently pivot around their insertion fulcrum. Both the arms 106 and the small arches 107 have their fulcrum so as to rotate around axes substantially parallel to a vertical or longitudinal axis of the patient's head.

At the two ends of each arch 107 there are two, optionally removable, rubber tips or pads 108, which rest on the patient's skin. Moreover, at the end of each arm 106 there is a slot 109 which allows to insert an optional (not shown) band, generally in a soft, bendable material, which surrounds the posterior part of the patient's head, so as to further immobilize her/him. The use of the band is optional and left to the preference of the individual human operator.

Figure 11:
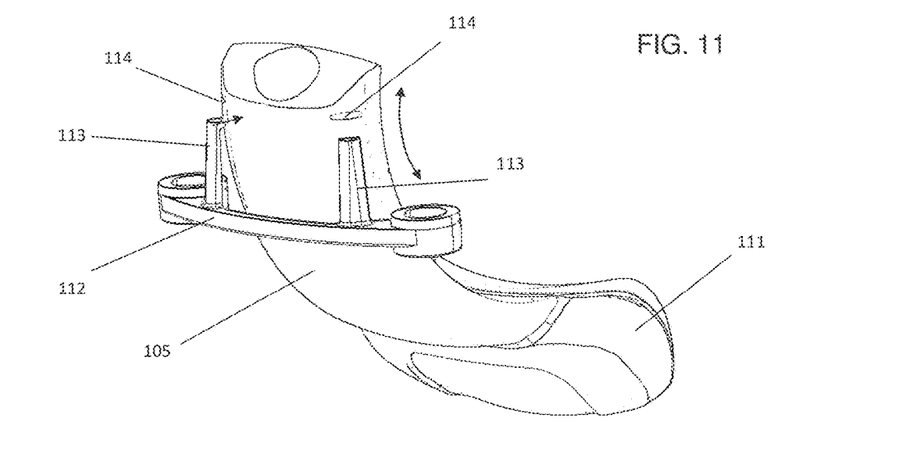
FIG. 11: Perspective view of a detail of the forehead support.

In FIG. 11 a detail of the forehead rest 105, sliding inside the (not shown) crossbeam 104 is shown. The forehead rest 105 has a particular arched profile, and ends in a wide rest surface 111, on which a small, optionally removable, cushion is fixed, made of a soft material (silicone, gum, foam) to improve the patient's comfort. The profile of rest surface 111 is slightly arched in order to better fit the patient's anatomy.

Inside the crossbeam 104, which was removed from FIG. 11 for the sake of clarity, there is an end-of-stroke device. The forehead rest 105 is free to slide inside the crossbeam 104, with two, one upper and one lower, limits. The lower limit is due to the fact that rest 111 is larger than the seat inside which forehead rest 105 slides. The upper limit is due to the end-of-stroke device 112, which is provided with two small teeth 113 which perform a slight constant friction on the forehead rest 105. The joint between teeth 113 and recesses 114 in the upper end of forehead rest 105 prevents the accidental extraction of the forehead rest 105. Nonetheless, all the assembly is designed so that an intentional pressure allows the extraction of the forehead rest 105 from its seat in the crossbeam 104 for cleaning, replacement, etc. Optional intermediate recesses can correspond to pre-defined positions of the forehead rest 105 if needed for particular acquisitions.

Figure 12:
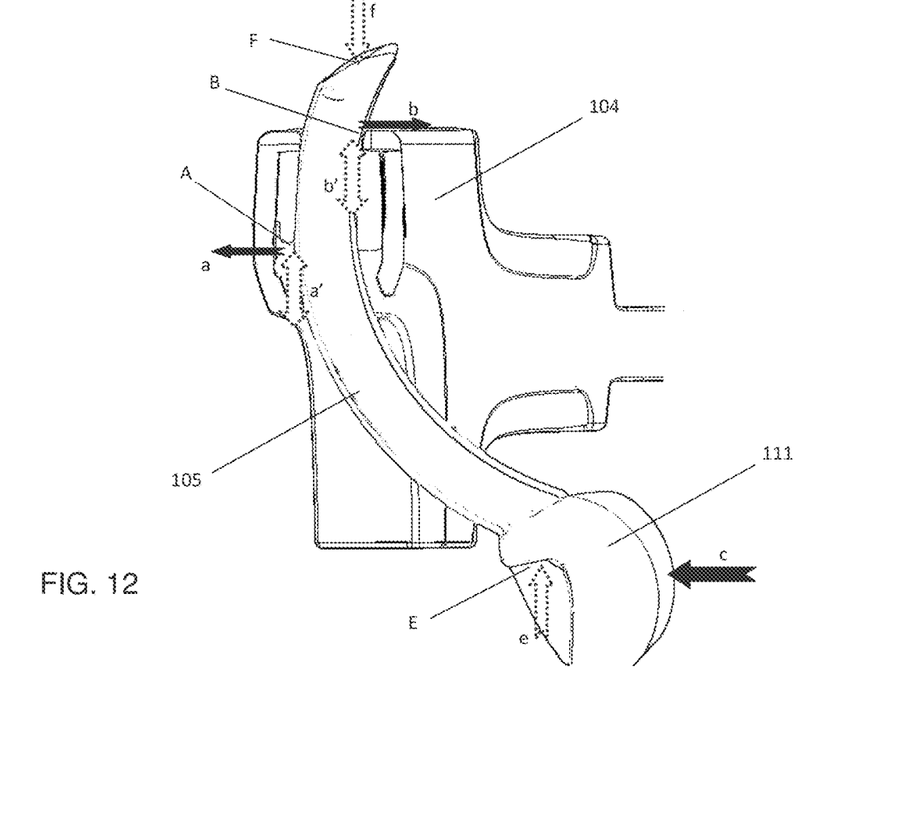
FIG. 12: Sagittal section of the forehead support inserted in the crossbeam.

FIG. 12 shows a sagittal section of the forehead rest 105 inserted in its seat in the crossbeam 104. It shows the working mechanism of the forehead rest 105. The working mechanism is highlighted in FIG. 12 through the bold and dotted arrows. Basically, when the patient rests her/his forehead on the rest surface 111, she/he applies a given pressure, represented by bold arrow c. The vector of the force has two components, shown by a and b arrows, in the two points A and B, thus blocking the sliding of the forehead rest 105 due to friction. On the other hand, when the fingers of the human operator act on points E and/or F, applying the pressures e and f, these have the two components represented by arrows a' and b', also in the points A and B. Therefore, the sliding of the forehead rest 105 is allowed inside its seat in the crossbeam 104. The profile of the forehead rest 105 is studied so that the mechanisms of blocking and sliding can work in any position said rest 105 can take while sliding inside its seat.

On the forehead rest 105 there are two recesses in the points E and F so as to precisely indicate to the human operator where to apply pressure when she/he wishes to height adjust the position of the forehead rest 105. It is apparent from the profile of the forehead rest 105 that its height adjustment occurs in the direction of thickness, too.

Figure 13:
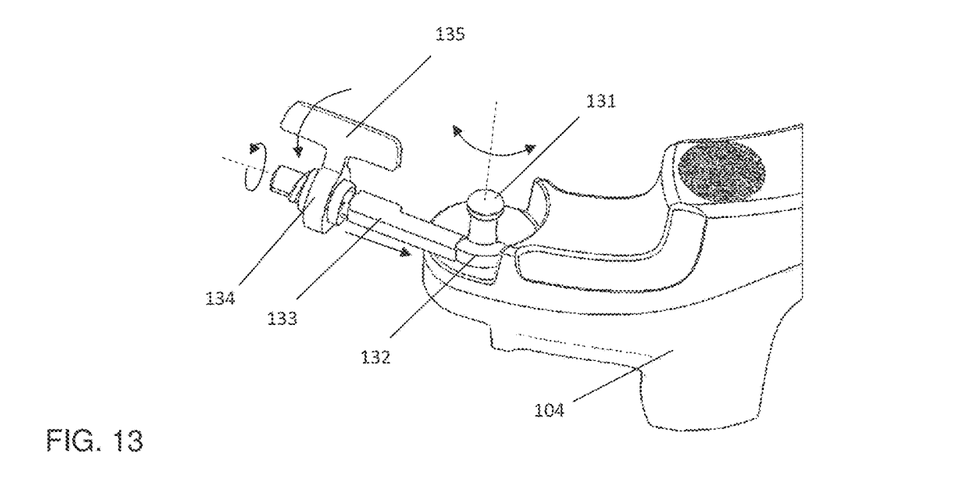
FIG. 13: Perspective view of a detail of the arm blocking mechanism.

FIG. 13 shows a detail of the blocking mechanism of arm 106, inside which there is inserted a ferrule or screw nut 134 leading the block screw 133. The arms 106 (not shown in this Figure) have their fulcrum on a pivot 131, and this allows to adjust them according to the width of the patient's cranium, width exhibiting a wide variability. When the blocking mechanism is activated, the block screw 133 enters into contact with block 132, integral with crossbeam 104, generating the friction needed for blocking the system. The block screw 133 is rotationally inserted in the ferrule 134, which is connected with the lever 135, protruding from the structure itself in order to be used by the human operator as controls through rotation of ferrule 134. The rotation of the ferrule, thanks to the thread and the fact that it is essentially stationary, entails an axial movement of the screw.

Figure 15A:
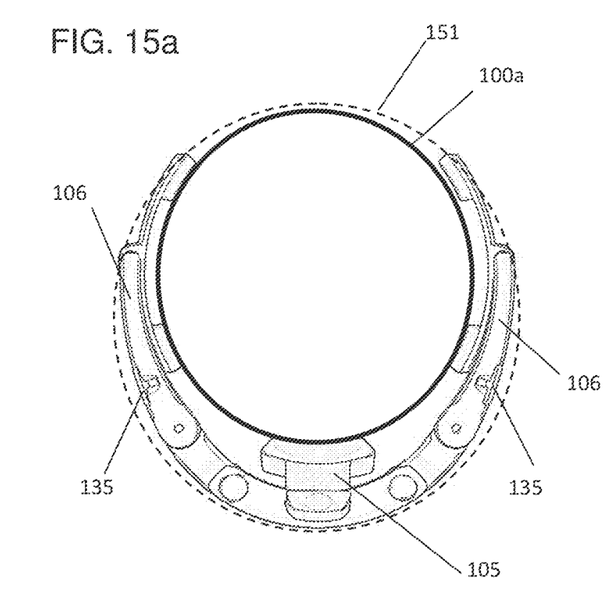
FIGS. 15a and Top view of two patients horizontal sections positioned in the 15b: craniostat, for a large patient (FIG. 15a) and a small patient (FIG. 15b).
Figure 15B:
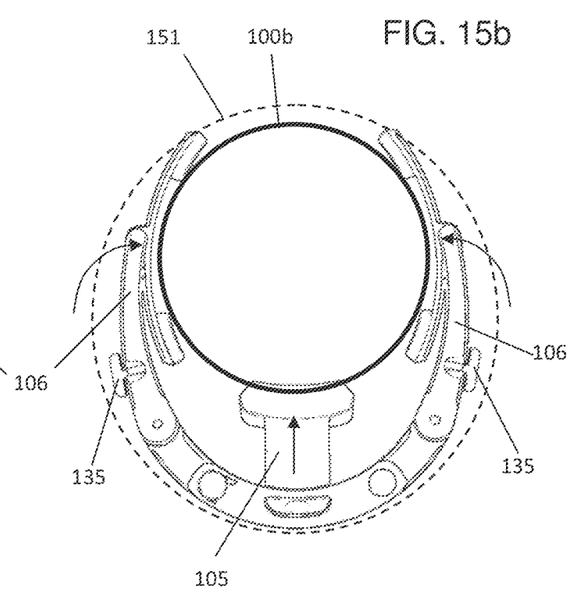

The lever 135 can rotate between two extreme positions, the first of which is shown in FIG. 10 (upwards) and the second of which is shown in FIG. 15b (outwards). When the lever 135 is in the upward position as shown in FIG. 10, the arm 106 is free to rotate around its pivot 131 without friction. On the other hand, when the lever 135 is rotate downwardly, it will block, meeting block 132, in any position comprised between the two extreme positions, position which is proportional to the width of the patient's cranium.

The human operator, after accommodating the patient inside the craniostat 20, adjusts the position of the arms 106 according to the patient's anatomy, and then rotates the levers 135 downwardly.

Figure 14:
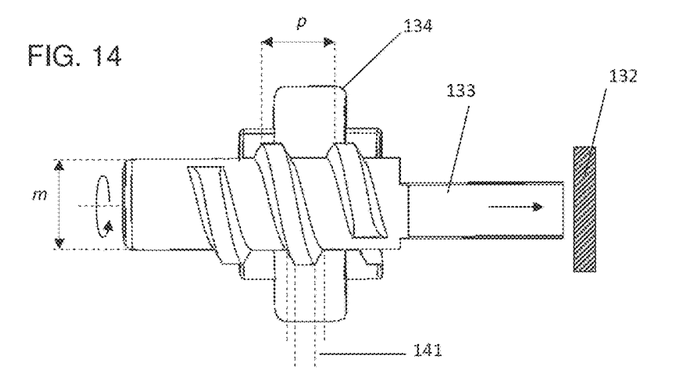
FIGS. 14, 14a Details of the working of the arm blocking mechanism, in and 14b: particular the overall blocking mechanism (FIG. 14), a wedge device (FIG. 14a), and a saw tooth device (FIG. 14b)

FIG. 14 shows in detail the working of the block mechanism of arms 106. The Figure shows a section along the rotation axis of the system ferrule 134-screw 133. The distance between the block screw 133 and the block 132 varies proportionally to the patient's anatomy. When the patient's cranium is small, and the distance screw 133-block 132 is therefore great, to reach the block a turn of the screw 133 will be needed which is wider than the turn of the screw needed with a big cranium, and this is ensured by the length of the thread of screw 133. When the block screw 133, pushed by the rotation of the ferrule, comes into contact with block 132, between the coupled faces of the ferrule 134 and of the screw thread 133 friction is generated, which blocks the arm 106. The block works only in the direction of opening the arms 106, because in the direction of closing there is the patient's head.

The section of the thread 141 is substantially a scalene trapezoid wherein the angles of the oblique surfaces working with the ferrule are different. The chosen angles, the lead p and the number of starts of the thread, and the diameter m of the screw 133, all cooperate to create a fluid movement when the human operator operates the lever 135; on the other hand, when the lever 135 is in the block position, proportional to the patient's anatomy, its friction is sufficient to block the patient.

FIG. 14 shows the preferred embodiment, based on a surface coupling system which blocks the moving parts by friction. However, based on the same principle there are many other possible embodiments, some of which are e.g. shown in FIGS. 14a and 14b.

Figure 14A:
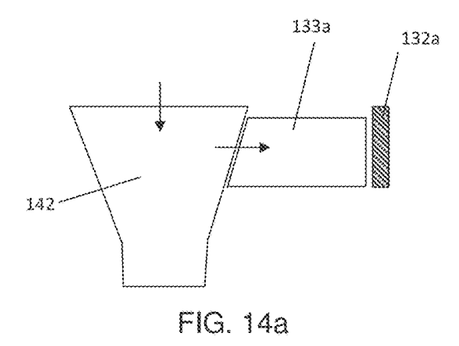

FIG. 14a shows a wedge device, wherein the movement of the rigid block 133a, conceptually equivalent to screw 133, is blocked by a wedge 142. According to the distance rigid block 133a-block 132a, the wedge 142 will be lowered of a variable quantity, proportional to the patient's anatomy.

Figure 14B:
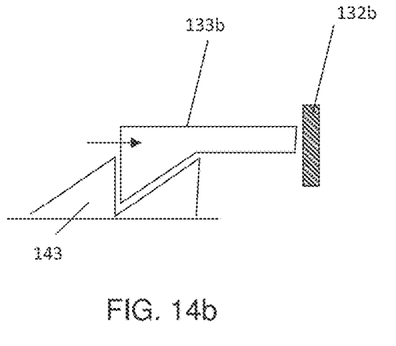

On the other hand, FIG. 14b shows a saw tooth device, wherein the movement of the rigid block 133b, conceptually equivalent to screw 133, is blocked by a specular saw tooth 143. The disadvantage of this configuration is that it works only discontinuously, and does not allow a continuous adjustment.

FIGS. 15a and 15b show the horizontal section of a cranium of a very large patient 100a and of a very small patient 100b, respectively. The comparison between the two Figures allows to appreciate the different position of forehead rest 105 and of arms 106. In particular, in FIG. 15a, forehead rest 105 is positioned upwardly, and thanks to its arched profile, protrudes little with respect to crossbeam 104. The arms 106 are in their maximal outward extension, and therefore the levers 135 are very near to their upward unblock position. Vice versa, in FIG. 15a, forehead rest 105 is positioned downwardly in its end-of-stroke position, and protrudes markedly towards the patient's forehead, while the arms 106 are in their inward maximal extension, and therefore the levers 135 are in their extreme block position, protruding outwardly.

In both FIGS. 15a and 15b the section of the anti-collision cylinder is represented by the dotted circumference 151. This allows to appreciate that, in the two extreme positions, even with a very large patient, the assembly patient-craniostat remains inside said cylinder. In particular, the space occupied by the levers 135, whose position is proportional to the patient's anatomy, is the same as the space freed through the closing of the arms 106 consequent to the inferior cranial diameter. In this way the assembly patient-craniostat remains always inside the anti-collision cylinder 151.

As already explained, the positioning needs are different for each acquisition (panoramic images; temporomandibular joints images; bite-wing images; three-dimensional images). In the following the method for patient positioning in the case of a panoramic acquisition is explained, which is probably the most articulate and common case. The human operator performs the following steps:

According to the image to be acquired, the human operator fixes the craniostat 20 on its support 30 in the radiographic apparatus 1; once it is positioned, she/he places the removable accessories (bite 54, chin rest 52); she/he positions the lever 53 in its unblocking position; she/he lifts the forehead rest 105; she/he completely opens the arms 106; she/he covers the bite 54 with a disposable protection and inserts it inside the hole 63 rotated toward one of the rods 23;

The operator accommodates the patient 100 inside the apparatus 1; the patient is asked to grab handles 9;

Firstly the operator adjusts the lower part 22 of the craniostat 20; the patient is asked to rest her/his chin on chin rest 52; the operator adjusts the height of the sliding column 4 to give the suitable inclination to the patient's head;

The patient is asked to open her/his mouth and the bite 54 is rotated and lowered until the anterior part 74 is in contact with her/his lower incisors (102);

The patient is asked to bite the bite 54 placing her/his incisors against the anterior part 74;

The operator blocks the bite 54 position using the lever 53; the block of the patient in the correct position is particularly easy for the operator, who needs to move the lever only, and for the patient, who is not obliged to squeeze in an apparatus 1 where the position of the bite is already fixed;

Successively the operator adjusts the upper part 21 of the craniostat 20; the operator adjusts the height of the crossbeam 104 sliding it on the rods 23; the operator lowers the forehead rest 105 so as to contact the patient's head; optionally the operator fixes an elastic band inside the slots 109 and also blocks the posterior part of the patient's head;

The operator adjusts the opening of the arms 106 so that arches 107 are in contact with the sides of the patient's cranium; once found the contact, she/he moves the levers 135 so as to block the arms 106 in a position which is comfortable for the patient.

Now the operator moves away from the apparatus 1 and X-ray emission can start.

While the invention has been described in connection with the above described embodiments, it is not intended to limit the scope of the invention to the particular forms set forth, but on the contrary, it is intended to cover such alternatives, modifications, and equivalents as may be included within the scope of the invention. Further, the scope of the present invention fully encompasses other embodiments that may become obvious to those skilled in the art and the scope of the present invention is limited only by the appended claims.

| SUMMARY OF REFERENCE NUMBERS | |
|---|---|
| 1 | extraoral apparatus |
| 2 | base |
| 3 | fixed column |
| 4 | sliding column |
| 5 | patient positioning |
| 6 | C-arm |
| 7 | X-ray generator |
| 8 | X-ray sensor |
| 9 | handles |
| 11 | teleradiography arm |
| 12 | teleradiography sensor support |
| 13 | teleradiography patient positioning |
| 15 | teleradioragraphy X-ray sensor |
| 20 | craniostat |
| 21 | craniostat upper portion |
| 22 | craniostat lower portion |
| 23 | rods |
| 30 | craniostat support |
| 41 | craniostat base |
| 45 | short pins |
| 46 | long pin |
| 52 | chin rest |
| 53 | lever |
| 54 | bite |
| 61 | bite stem |
| 62 | block |
| 63 | hole |
| 64 | spring |
| 71 | bitewing recess |
| 72 | small lever |
| 73 | spring |
| 74 | anterior part |
| 75 | posterior part |
| 76 | arched part |
| 77 | recess on arched part |
| 78 | ribs |
| 81 | precise pin |
| 82 | loose pin |
| 90 | nose support |
| 91 | precise pin |
| 92 | loose pin |
| 93 | recess |
| 100 | patient |
| 100a | big patient |
| 100b | small patient |
| 101 | upper incisors |
| 102 | lower incisors |
| 103 | Welander curve |
| 104 | crossbeam |
| 105 | forehead rest |
| 106 | arm |
| 107 | arch |
| 108 | rubber tips |
| 109 | band slot |
| 111 | forehead rest surface |
| 112 | end-of stroke device |
| 113 | teeth |
| 114 | recess |
| 131 | pivot |
| 132 | block |
| 133 | block screw |
| 133a | rigid block |
| 133b | rigid block |
| 134 | ferrule or screw nut |
| 135 | lever |
| 141 | thread profile |
| 142 | wedge |
| 143 | saw tooth |
| 151 | anti-collision cylinder |

The invention claimed is:

1. A craniostat for an extraoral dental radiographic apparatus comprising:
   an upper portion; and
   a lower portion connected to the upper portion by two rods,
   wherein the upper portion comprises a rest for a patient's forehead, wherein the forehead rest has an arched arm and a forehead support surface connected thereto, the arm vertically sliding in a rest seat inside a crossbeam supported by the rods, and wherein the rest seat is shaped as an opening in the crossbeam, within which the arm is slidingly inserted.

2. The craniostat according to claim 1, wherein a stop of the forehead rest at a desired height occurs by shape friction, due to resolution of forces caused by the arm of the forehead rest inside the seat, further comprising means for blocking disposed in the upper portion, the means for blocking causing the arm to become blocked within the seat when the patient's forehead is pushed against the forehead rest, and to be slidable within the seat when the patient's forehead is released from the forehead rest.

3. The craniostat according to claim 1, wherein the arm extends in an anterio-posterior direction, whereby a movement of the arm within the rest seat causes the forehead support surface to move also in a sagittal direction, from the patient's forehead to a back of the patient's head.

4. The craniostat according to claim 3, wherein a movement of the forehead rest is upwardly limited by a dimension of the forehead support surface and downwardly by an end-of-stroke device comprising two teeth on the rest seat and two recesses on the arm.

5. The craniostat according to claim 4, wherein the forehead rest is removable from the rest seat by downward pressure, which allows an extraction of the arm from the end-of-stroke device.

6. The craniostat according to claim 1, wherein, when a patient has a cranium of smaller dimensions, said forehead rest is configured to slide toward a back of the patient's head, with a distance between the patient's forehead and the crossbeam (104) which is longer than for a patient having a cranium of larger dimensions.

7. The craniostat according to claim 1, wherein, at two ends of the crossbeam, two slots are defined, configured to have an elastic band inserted therein for further optional immobilization of a posterior part of the patient's head.

8. The craniostat according to claim 1, wherein the upper portion is made exclusively of a radiolucent plastic material, free of metal.

9. A method of positioning a patient in an extraoral dental radiographic apparatus comprising the following steps:
providing the apparatus with a craniostat according to claim 1;
having a human operator accommodate a patient (100) in said apparatus (1);
having said human operator adjust the craniostat, so that a lower portion of the craniostat is aligned with the patient;
asking the patient to bite a bite,
having said operator adjusts a height of a crossbeam by sliding said crossbeam on rods; and
lowering the patient's forehead rest so as to contact the patient's forehead.

10. The method of positioning a patient in an extraoral dental radiographic apparatus according to claim 9, further comprising the step of immobilizing the patient's back of the head with an elastic band inserted in slots at two ends of the crossbeam.

11. The craniostat according to claim 1, further comprising two rest members (107) for lateral sides of the patient's head, the two rest members being pivotally engaged at opposite end portions of the crossbeam.

* * * * *